(12) United States Patent (10) Patent No.: US 7,611,012 B2
Ross (45) Date of Patent: Nov. 3, 2009

(54) INSULIN SYRINGE STORAGE RACK

(76) Inventor: Michelle Ross, W158 S7349 Martin Dr., Muskego, WI (US) 53250

( * ) Notice: Subject to any disclaimer, the term of this patent is extended or adjusted under 35 U.S.C. 154(b) by 22 days.

(21) Appl. No.: 11/858,875

(22) Filed: Sep. 20, 2007

(65) Prior Publication Data
US 2009/0026108 A1 Jan. 29, 2009

Related U.S. Application Data

(63) Continuation-in-part of application No. 11/782,131, filed on Jul. 24, 2007.

(51) Int. Cl.
*B65D 83/10* (2006.01)
(52) U.S. Cl. .................. 206/366; 206/433; 206/571; 211/60.1
(58) Field of Classification Search ......... 206/364–366, 206/570–572, 438, 443, 564, 369; 211/60.1, 211/74, 85.13; 604/187, 192, 218
See application file for complete search history.

(56) References Cited

U.S. PATENT DOCUMENTS

| | | | | |
|---|---|---|---|---|
| 4,237,906 A | * | 12/1980 | Havstad et al. | 600/556 |
| 4,850,484 A | * | 7/1989 | Denman | 206/366 |
| 4,863,023 A | | 9/1989 | Payne et al. | |
| 5,184,721 A | * | 2/1993 | Wengyn et al. | 206/366 |
| 5,190,169 A | * | 3/1993 | Sincock | 211/60.1 |
| 5,217,694 A | | 6/1993 | Gibler et al. | |
| 5,396,989 A | * | 3/1995 | Hein | 206/366 |
| 5,431,201 A | | 7/1995 | Torchia et al. | |
| 5,823,363 A | * | 10/1998 | Cassel | 211/60.1 |
| 5,850,917 A | * | 12/1998 | Denton et al. | 206/366 |
| 6,540,072 B1 | | 4/2003 | Fischer | |
| 6,955,259 B1 | | 10/2005 | Jesse | |
| 6,959,814 B1 | | 11/2005 | Hyman | |
| 2004/0074795 A1 | | 4/2004 | Fischer | |

FOREIGN PATENT DOCUMENTS

EP 0790063 B1 10/2002

* cited by examiner

*Primary Examiner*—Luan K Bui
(74) *Attorney, Agent, or Firm*—Jill Gilbert Welytok

(57) ABSTRACT

An insulin syringe storage rack comprised of: a first side surface and a second side surface, both being substantially vertical and having a top edge; a top surface being substantially horizontal and supported by the first and second side surfaces; a plurality of apertures positioned on the top surface and sized to receive an insulin syringe; and a plurality of tubular structures, each positioned below the top surface and corresponding to one of the apertures and adapted to receive and vertically support said insulin syringe. Alternate embodiments of the insulin syringe storage rack can further include one or more additional storage receptacles a front side surface and/or a rear side surface, and space for disposing indicia thereon.

5 Claims, 4 Drawing Sheets

US 7,611,012 B2

INSULIN SYRINGE STORAGE RACK

CROSS-REFERENCE TO RELATED APPLICATIONS

This application claims the benefit of and priority to U.S. non-provisional application Ser. No. 11/782,131, filed on 24 Jul. 2007 and incorporated herein in its entirety.

FIELD OF INVENTION

This invention relates generally to the field of syringe storage, and specifically to a rack for storing insulin syringes within a refrigerator.

BACKGROUND

Figure 1:
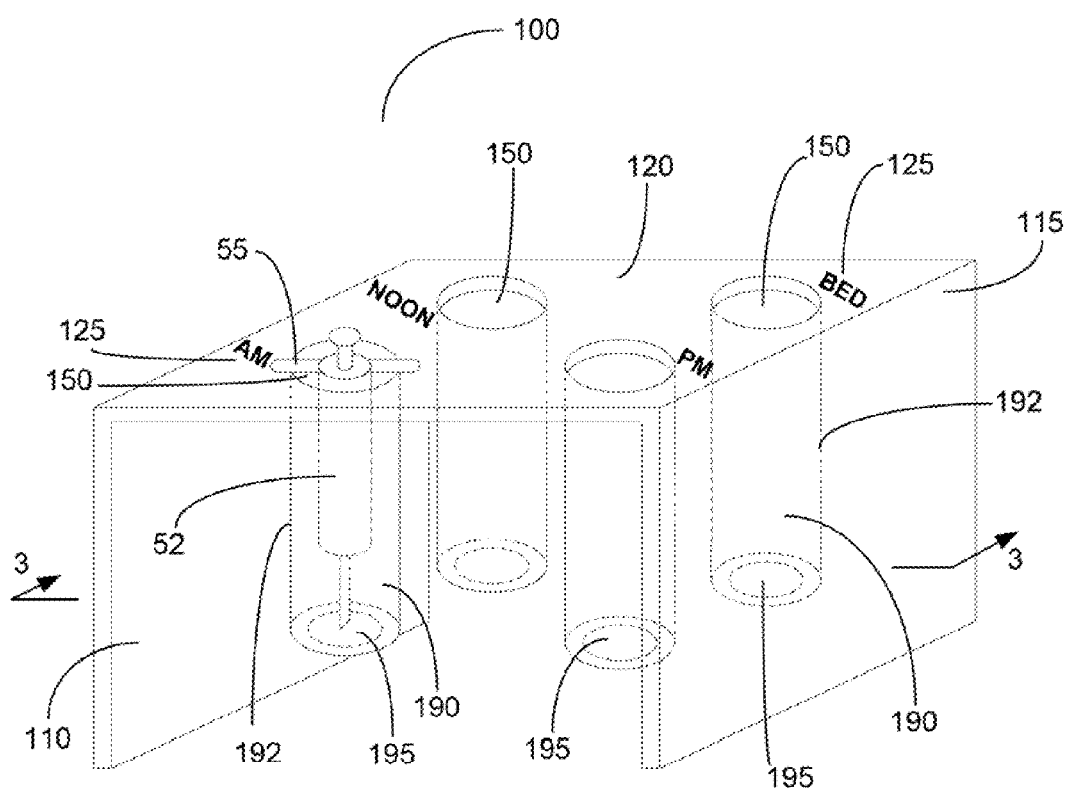
FIG. 1 shows a top perspective view of one embodiment of the insulin syringe storage rack.

Given the present-day motivation to decrease and contain healthcare related costs, it is desirable to develop new methods and apparatuses for minimizing the cost of treatment. Such minimization of costs often includes self-treatment for those with conditions that allow the patient to treat himself or herself without requiring a visit to an office or a health care provider to attend the patient in his or her home.

One disease that allows some self-treatment is diabetes mellitus, types I and II. Diabetes requires, among other things, insulin injections to control the disease, especially for type-I diabetes.

In 2006, according to the World Health Organization, at least 171 million people worldwide suffer from diabetes mellitus. Its incidence is increasing rapidly, and it is estimated that by the year 2030, this number will double. Furthermore, diabetes prevalence increases with age, and the numbers of older persons with diabetes are expected to grow as the elderly population increases in number. According to the American Diabetes Association, approximately 18.3% (8.6 million) of Americans age 60 and older have diabetes. The National Health and Nutrition Examination Survey (NHANES III) demonstrated that, in the population over 65 years old, almost 18% to 20% have diabetes.

With such a large number of insulin users being elderly, there exists a need in the art for an apparatus (e.g., a rack) which will receive and hold various sizes of medical syringes that have been pre-filled with insulin, and that can further facilitate easy recognition of whether the syringe has been used at the proper time. A typical insulin syringe is specially sized and has dimensions to hold 30 units, 50 units, and 100 units of insulin.

As used herein, the term "syringe" refers to any small device narrowed at its outlet and fitted with either a piston or a rubber bulb for drawing in a quantity of fluid or for injecting fluid (e.g., insulin) into the body, whether made of glass, metal, or hard rubber.

As used herein, the term "refrigerator" refers to any appliance, cabinet, or room for storing food or another substances at a low temperature, and this term may be used to refer to a specific area of the refrigerator such as a shelf, butter compartment, side storage area (traditionally used for condiments), or a rack. It is contemplated that the invention described herein may be specially adapted for fit and stabilization on a specific rack, shelf, compartment, or side shelf of a refrigerator.

DETAILED DESCRIPTION OF EMBODIMENTS OF THE INVENTION

For the purpose of promoting an understanding of the present invention, references are made in the text hereof to embodiments of an insulin syringe storage rack, only some of which are depicted in the figures. It should nevertheless be understood that no limitations on the scope of the invention are thereby intended. One of ordinary skill in the art will readily appreciate that modifications such as the dimensions, size, and shape of the components, alternate but functionally similar materials from which the insulin syringe storage rack is made, and the inclusion of additional elements are deemed readily apparent and obvious to one of ordinary skill in the art, and all equivalent relationships to those illustrated in the drawings and described in the written description do not depart from the spirit and scope of the present invention. Some of these possible modifications are mentioned in the following description. Therefore, specific details disclosed herein are not to be interpreted as limiting, but rather as a basis for the claims and as a representative basis for teaching one of ordinary skill in the art to employ the present invention in virtually any appropriately detailed apparatus or manner.

It should be understood that the drawings are not necessarily to scale, emphasis instead being placed upon illustrating the principles of the invention. In addition, in the embodiments depicted herein, like reference numerals in the various drawings refer to identical or near indentical structural elements.

Moreover, the term "substantially" or "approximately" as used herein may be applied to modify any quantitative representation that could permissibly vary without resulting in a change in the basic function to which it is related. For example, one embodiment of the insulin syringe storage rack is disclosed herein as orienting the syringe vertically. The insulin syringe storage rack might permissibly orient the syringe non-vertically and still be within the scope of the invention if its functionality is not materially altered.

Referring now to the drawings, FIG. 1 shows a top perspective view of one (1) embodiment of insulin syringe storage rack 100. Insulin syringe storage rack 100 is comprised of top surface 120, first side surface 110, second side surface 115, and tubular support structures 190. First side surface 110 and second side surface 115 are vertically positioned and support top surface 120, which is horizontally positioned. Integrally molded to top surface 120 are four (4) tubular support structures 190, each of which includes sidewall 192. In the embodiment shown, top surface 120 includes four (4) apertures 150, each of which allows access to one (1) tubular support structure 190.

In the embodiment shown, each sidewall 192 of tubular support structure 190 is generally tubular, but can be of almost any alternate shape, e.g. multi-faceted, and has an open bottom (designated 195). Open bottom 195 allows tubular support structures 190 to be easily cleaned. However, it should be understood that tubular support structures 190 could, alternately, be closed, either with a flat, rounded, or other-shaped bottom, or can be partially closed. Each syringe 50 fits within one (1) tubular support structure 190, but is shorter than the length of tubular support structure 190. The diameter of tubular support structure 190 is slightly wider than the width of syringe body 52, but less than the diameter of finger tabs 55, thus allowing syringe 50 to be supported within tubular support structure 190, but also easily removed. In the embodiment shown in FIG. 1, each tubular support structure 190 has an inner diameter of one half inch (½") (see FIG. 3). This diameter is just large enough to allow syringe 50 to be positioned in tubular support structure 190, but to minimize the amount of possible lateral movement of each syringe 50 within tubular support structure 190, thus minimizing the chance of damaging syringe 50. However, it should be understood that tubular support structure 190 could have alternate dimensions to facilitate use of syringe storage rack 100 with other sizes of syringes 50, whether standard or custom sizes.

In the embodiment shown, tubular structures 190 are vertically oriented, as are any syringes 50 positioned within insulin syringe storage rack 100. However, in an alternate embodiment of insulin syringe storage rack 100, tubular structures 190 are angled such that each aperture 150 is forward of bottom 195 of tubular structure 190, thus orienting the top of syringe 50 forward and allowing easier removal of syringe 50.

Also in the embodiment of syringe storage rack 100 shown in FIG. 1, top surface 120 includes a gap between each aperture 150. Specifically, in the embodiment shown, there is a one half inch (½") gap between apertures 150 and between apertures 150 and the front and rear edges of top surface 120. There is also a one inch (1") space between apertures 150 and the right and left edges of top surface 120 (i.e., between apertures 150 and side surfaces 110, 115. These gaps and spaces, whether between apertures 150 or between apertures 150 and the side edges, provides room for the user to place a sticker, write with a writing utensil capable of writing on syringe storage rack 100 (e.g., a permanent marker or a grease pencil), for information to be printed, or for syringe storage rack 100 to be manufactured with writing in the gaps and spaces. Such information is collectively referred to herein as "indicia 125."

In these spaces and gaps can be written use instructions or other indicia 125. Specifically, the embodiment of insulin syringe storage rack 100 shown in FIG. 1 is designed to support four (4) insulin syringes, or one (1) day's use. For example, indicia 125 can indicate "A.M.," "Noon," "P.M.," and "Bed" adjacent to each aperture 150, indicating that one (1) syringe 50 should be used in the morning, noontime, evening, and at bedtime. This allows the user to ascertain whether a dose has been taken at the appropriate time, avoiding missing a dose or taking too doses too frequently. It should be understood, however, that alternate instructions or indicia could be included in the gaps between apertures 150 or in the space between apertures 150 and either side edge. It should further be understood that different sized spaces or gaps can be used, depending on the need for instructions or other indicia 125 and that the gaps and/or spaces need not be identical between each and every aperture 150 or between aperture 150 and side edges.

In addition, alternate embodiments of insulin syringe storage rack 100 can include any number of tubular structures 190 to accommodate any number of syringes 50. For example, one (1) alternate embodiment of insulin syringe storage rack 100 has twenty-eight (28) apertures 150 and tubular structures 190, arranged in a seven (7) by four (4) grid, corresponding to seven (7) days in a week and four (4) doses per day. Specifically, this alternate embodiment of syringe storage rack 100 can be used by a person needing four (4) doses a day over the course of a week, in which indicia 125 could indicate "A.M.," "Noon," "P.M.," and "Bed," along the left side of top surface 120, and "Sunday," "Monday," "Tuesday," "Wednesday," "Thursday," "Friday," and "Saturday" between apertures 150 and the front edge of top surface 120, indicating that one (1) syringe 50 from each row should be used in the morning, noontime, evening, and at bedtime, each day of the week.

Because insulin must be refrigerated, syringe storage rack 100 is intended to be placed within a refrigerator (not shown). As such, syringe storage rack 100 is made of a material that will not deform, become brittle, or significantly constrict in size (either the dimensions of syringe storage rack 100 or of apertures 150) The embodiments shown and described herein are made of plastic, but can also be made of wood, metal (e.g., steel, stainless steel, aluminum), glass, or any other material commonly known and used in the art, including combinations thereof.

Figure 2:
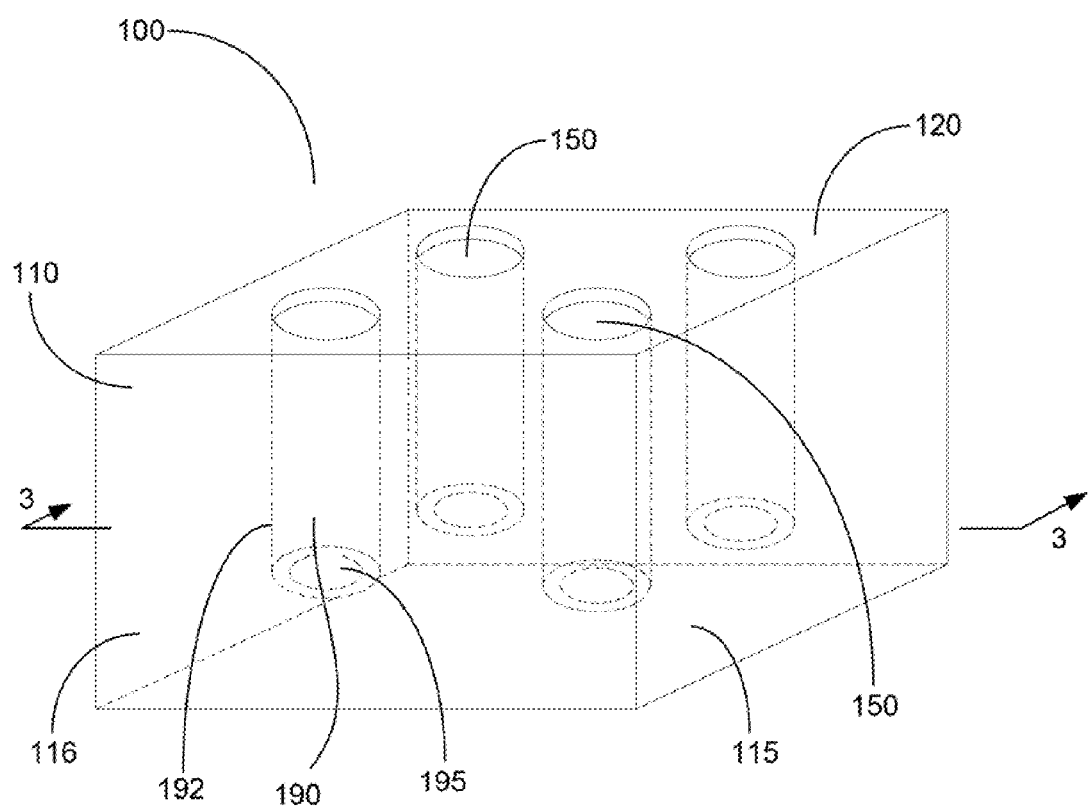
FIG. 2 shows a top perspective view of one alternate embodiment of the insulin syringe storage rack.

FIG. 2 shows a top perspective view of an alternate embodiment of insulin syringe storage rack 100 in which insulin syringe storage rack 100 further includes front side surface 116 and a rear side surface (not visible), but still an open bottom. Such an embodiment may provide a more aesthetically pleasing appearance in that insulin syringe storage rack 100 would appear substantially solid and tubular structures 190 would not be seen when insulin syringe storage rack 100 is viewed from the front.

Figure 3:
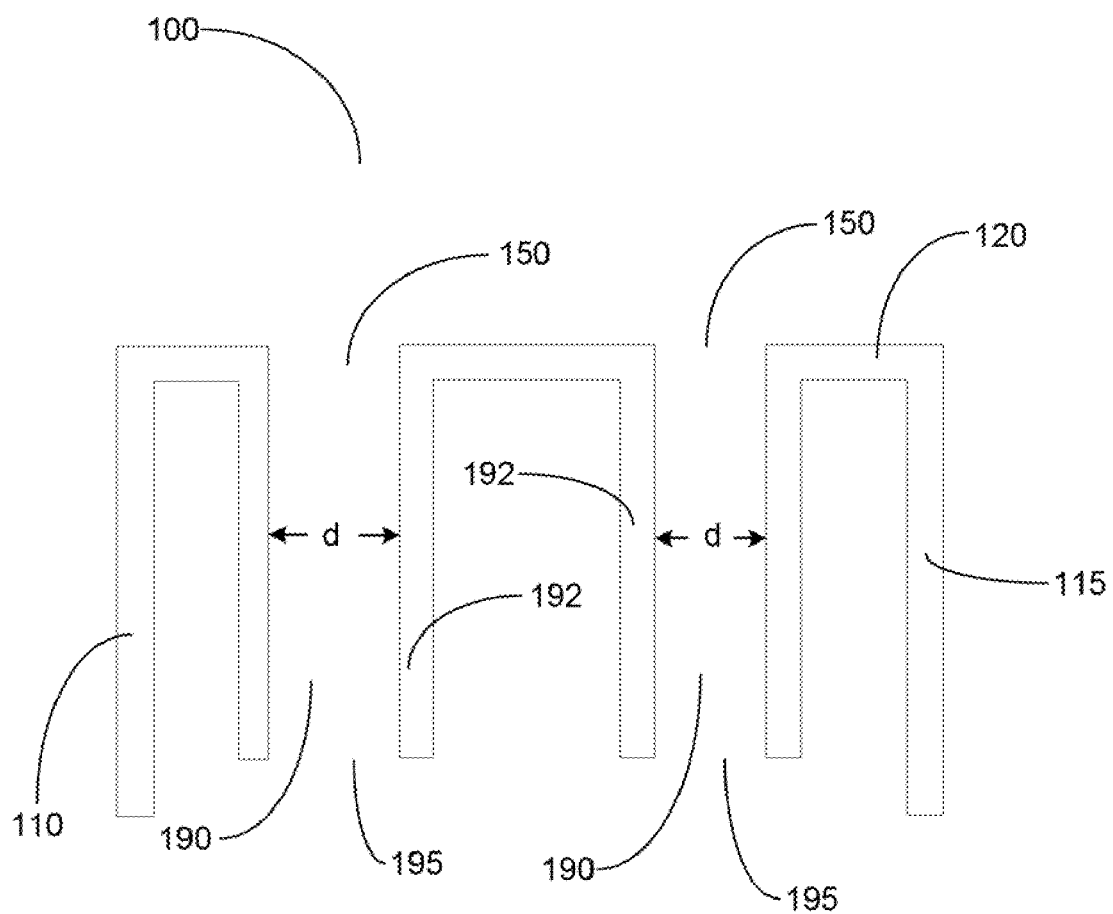
FIG. 3 shows a cross-sectional view of the embodiment of the insulin syringe storage rack shown in FIG. 1, taken along line 3-3.

FIG. 3 shows a cross-sectional view of the embodiment of insulin syringe storage rack 100 shown in FIG. 1, taken along line 3-3. As can be seen, top surface 120 is supported by side surfaces 110, 115 and includes apertures 150 and corresponding tubular structures 190. As provided supra, the inner diameter d of each tubular structure is one half inch (½") to accommodate the syringe (not shown). Because the only difference between the embodiment of insulin syringe storage rack 100 shown in FIG. 1 and FIG. 2 is the presence of front side surface 116 and the rear side surface, FIG. 3 also shows a cross-sectional view of the embodiment of insulin syringe storage rack 100 shown in FIG. 2.

Figure 4:
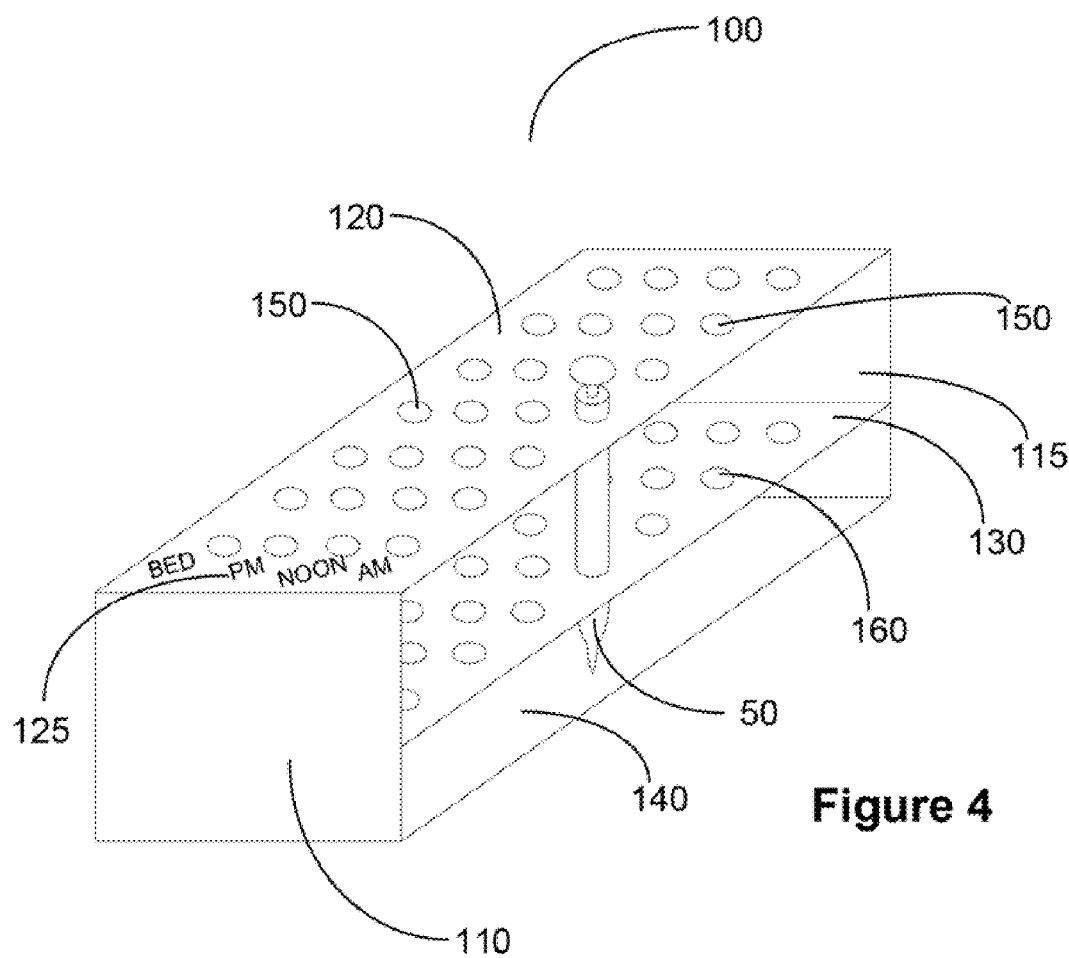
FIG. 4 shows a top perspective view of one alternate embodiment of the insulin syringe storage rack.

FIG. 4 shows a top perspective view of one alternate embodiment of insulin syringe storage rack 100. As can be appreciated, insulin syringe storage rack 100 is comprised of first side surface 110, second side surface 115, top surface 120, middle layer 130, and bottom layer 140. Top surface 120, middle layer 130, and bottom layer 140 each extend from first side surface 110 to second side surface 111. Furthermore, top surface 120 and middle layer 130 each have a series of apertures 150, 160 disposed thereon, with each aperture 150 on top surface 120 having a corresponding aperture 160 on middle layer 130.

As can be seen, syringe 50 fits within one (1) aperture 150 on top surface 120 and one (1) aperture 160 on middle layer 130, thus vertically orienting syringe 50. However, in an alternate embodiment of insulin syringe storage rack 100, apertures 150 on top surface 120 are slightly offset forward from the corresponding aperture 160 on middle layer 130. In such an embodiment, syringe 50 would be angled slightly forward to allow potentially more easy removal of syringe 50. In still further alternate embodiments of insulin syringe storage rack 100, one (1) or more additional horizontal layers (not shown) can be added to increase the stability of insulin syringe storage rack 100 and/or of syringe 50 within insulin syringe storage rack 100. Such additional horizontal support layers would further include corresponding apertures therein to allow syringes 50 to pass therethrough. Moreover, it should be understood that the additional horizontal support layer can, but need not, extend the entire length of insulin syringe storage rack 100. That is, the additional horizontal support layer can be used to support only a portion of syringes 50 as needed, but not need not support all.

Bottom layer 140 is substantially solid to support syringe(s) 50. In the embodiment shown, bottom layer 140 is flat, but one (1) alternate embodiment of syringe storage rack 100 comprises bottom layer 140 further including one (1) or more depressions (not shown), into which the bottom (typically the needle portion) of syringe 50 can be positioned, to further maintain syringe 50 in its substantially vertical position. In an embodiment of syringe storage rack 100 in which apertures 150, 160 are slightly offset to orient syringe 50 forward, the depressions on bottom layer 140 would similarly be offset, i.e., aligned with apertures 150, 160.

In the alternate embodiment shown in FIG. 4, syringe storage rack 100 is seven and one half inches (7½") long (i.e., between side surfaces 110, 115), each side surface 110, 115 is a four inch (4") square, and middle layer 130 is one and one half inches (1½") above bottom layer 140. Thus, because syringe storage rack 100 is four inches (4") high, there is also two and one half inches (2½") space between middle layer 130 and top surface 120. However, it should be understood that syringe storage rack 100 could be of almost any dimensions, depending on the size and the number of syringe(s) 50 to be held by syringe storage rack 100.

Furthermore, in the embodiment of syringe storage rack 100 shown in FIG. 4, each aperture 150, 160 is one half inch (½") wide, allowing syringe 50 to be positioned in apertures 150, 160, but to minimize the amount of possible movement of each syringe 50 within apertures 150, 160. However, it should be understood that apertures 150, 160 could have alternate dimensions to facilitate use of syringe storage rack 100 with other sizes of syringes, whether standard or custom sizes. In the embodiment of syringe storage rack 100 shown, there are four (4) rows of seven (7) apertures 150 in top surface 120 and a corresponding number of apertures 160 in middle layer 130. Although not shown in this embodiment, if bottom layer 140 further includes depressions (not shown; discussed in detail supra), a corresponding number of depressions would also be included. However, one of ordinary skill in the art will recognize that any grid pattern having different numbers of rows and/or columns can be used.

Also in the embodiment of syringe storage rack 100 shown in FIG. 4, top surface 120 includes a gap between each aperture 150, 160. Specifically, in the embodiment shown, there is a one half inch (½") gap between apertures 150 and between apertures 150 and the front and rear edges of top surface 120. There is also a one inch (1") space between apertures 150 and the right and left edges of top surface 120 (i.e., between apertures 150 and side surfaces 110, 115. These gaps and spaces, as with the embodiment shown and described with respect to FIG. 1, provides room for indicia 125. Specifically, the embodiment of insulin syringe storage rack 100 shown in FIG. 4 is for use by a person needing four (4) doses a day over the course of a week in which indicia 125 indicate "A.M.," "Noon," "P.M.," and "Bed," along the left side of top surface 120. Although not shown, top surface 120 can further include, for example, "Sunday," "Monday," "Tuesday," "Wednesday," "Thursday," "Friday," and "Saturday" between apertures 150 and the front edge of top surface 120, thus allowing the user to ascertain whether a dose has been taken at the appropriate time, avoiding missing a dose or taking too doses too frequently. It should be understood, however, that as with all alternate embodiments of insulin syringe storage rack 100, instructions or other indicia 125 could be included in the gaps between apertures 150 or in the space between apertures 150 and either side edge and that different sized spaces or gaps can be used, depending on the need for instructions and that the gaps and/or spaces need not be identical between each and every aperture 150 or between aperture 150 and side edges.

Figure 5:
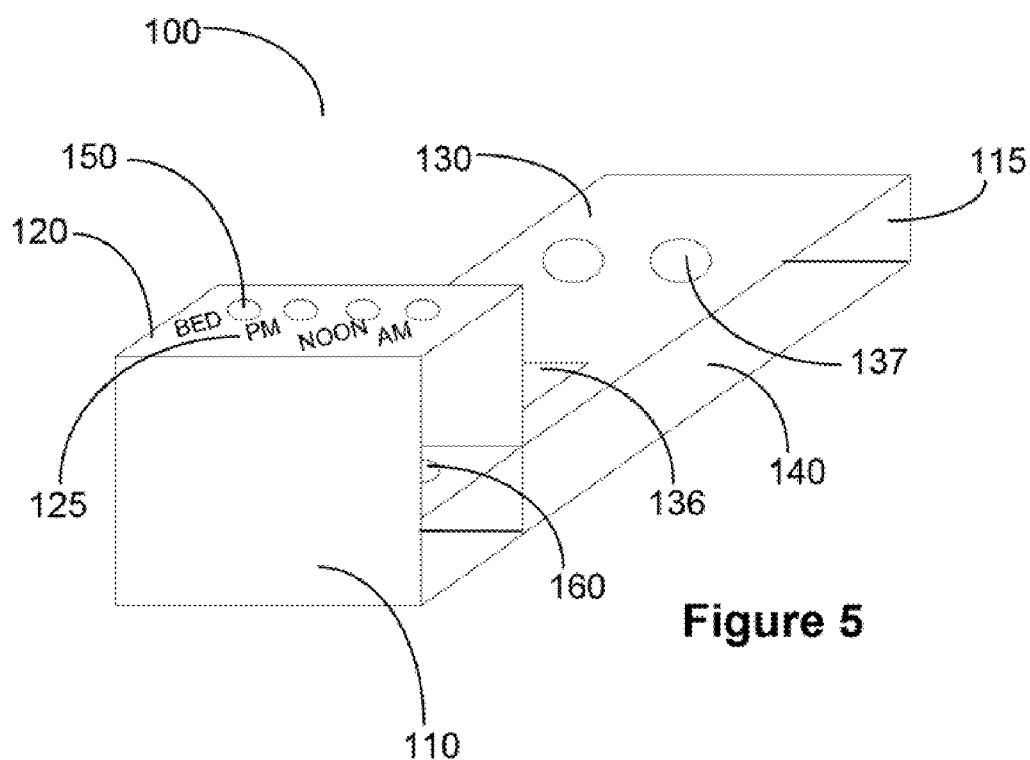
FIG. 5 shows a top perspective view of one alternate embodiment of the insulin syringe storage rack.

FIG. 5 shows a top perspective view of an alternate embodiment of insulin syringe storage rack 100 in this embodiment, top surface is only one and one half inches (½") wide and has a single row of apertures 150. Syringe storage rack 100 still has the same overall length, height, and width, but the height is four inches (4") for only that portion of syringe storage rack 100 that has both top surface 120 and middle layer 130. Syringe storage rack 100 is only one and one half inches (1½") high for that portion of syringe storage rack 100 that does not include top surface 120. In effect, middle layer 130 functions as both the middle layer (for that portion under top surface 120) and as a topmost layer. Such a construction of syringe storage rack 100 is intended for a single day's use. In such an embodiment fewer apertures 150 and room for instructions would be necessary. Syringe storage rack 100 could be made with less material and thus less expensively. One of ordinary skill in the art will recognize that such a multi-tiered construction can include any number of apertures 150, 160, and that the taller portion of syringe storage rack 100 can be in the middle or rightmost side of syringe storage rack 100. In addition, syringe storage rack 100 can include two (2) taller portions, one (1) on each side with a shorter portion in between.

In the embodiment shown in FIG. 5, middle layer 130 can further include additional means for storing related materials. For example, apertures 137 can be used for holding an alcohol jar (not shown) and recess 136 can be used for holding cotton balls. However, it should be understood that these additional storage receptacles can also be used for holding and storing insulin packaging, insulin boxes, insulin vials, swabs, adhesive bandages, testing equipment, glucometers, empty syringes, unused syringes, physician's instructions, phone numbers, a list of medical symptoms, emergency information, a writing instrument, or any other related object(s), including combinations thereof.

Referring again to FIG. 1, as with the embodiment of insulin syringe storage rack 100 shown and described with respect to FIG. 5, the embodiment of insulin syringe storage rack 100 shown in FIGS. 1 and 2 can also further include the additional means for storing related materials such as additional apertures and/or recesses (not shown), for holding, for example, an alcohol jar, cotton balls, insulin packaging, insulin boxes, insulin vials, swabs, adhesive bandages, testing equipment, glucometers, empty syringes, unused syringes, physician's instructions, phone numbers, a list of medical symptoms, emergency information, a writing instrument, or any other related object(s), including combinations thereof.

While the insulin syringe storage rack has been shown and described with respect to several embodiments and uses in accordance with the present invention, it is to be understood that the same is not limited thereto, but is susceptible to numerous changes and modifications as known to a person of ordinary skill in the art, and it is intended that the present invention not be limited to the details shown and described herein, but rather cover all such changes and modifications obvious to one of ordinary skill in the art.

I claim:

1. A mildew resistant syringe storage rack system adapted for insulin syringes to store a plurality of pre-drawn insulin dosages in a refrigerator comprised of:

a first side surface, said first side surface being vertical and having a first top edge;

a second side surface, said second side surface being vertical and having a second top edge;
a horizontal top surface, said horizontal top surface extending between said first side surface and said second side surface at said first top edge of said first side surface and said second top edge of said second top edge;
at least one insulin syringe having a first finger tab and a second finger tab wherein said first finger tab and said second finger rest on said horizontal top surface, said first finger tab and said second finger tab equally supporting the weight of said at least one insulin syringe;
a plurality of non-tapered tubular structures positioned below said horizontal top surface, each of said plurality of tubular structures adapted to receive said at least one insulin syringe;
each of said plurality of tubular structures having a top opening and a bottom opening, said top opening and said bottom opening allowing the flow of air through each of said plurality of tubular structures; and
said plurality of tubular structures are of a sufficient diameter directly proportional to the circumference of said at least one insulin syringe, and of a diameter less than the widest point of said finger tabs of said at least one insulin syringe and which minimizes lateral movement of said syringes regardless of the size of said insulin syringe to minimize the contact of said at least one insulin syringe with the sides of said tubular structure.

2. The syringe storage rack system of claim 1, wherein said syringe storage rack further includes one or more additional storage receptacles for receiving at least one medical object selected from a group consisting of an alcohol jar, insulin packaging, an insulin box, an insulin vial, a swab, cotton balls, an adhesive bandage, testing equipment, a glucometer, an empty syringe, an unused syringe, a physician's instructions, a phone number, a list of medical symptoms, emergency information, a writing instrument, and combinations thereof.

3. The syringe storage rack system of claim 1, wherein said syringe storage rack system further includes at least one of a front side surface and a rear side surface.

4. The syringe storage rack system of claim 1, wherein said syringe storage rack is made of a material selected from a group consisting of plastic, metal, wood, and combinations thereof.

5. The syringe storage rack system of claim 1, wherein said horizontal top surface further includes at least one space for disposing indicia thereon, said indicia being selected from a group consisting of a writing, a printing, and at least one label.

* * * * *